(12) United States Patent
Anderson et al.

(10) Patent No.: US 6,174,868 B1
(45) Date of Patent: *Jan. 16, 2001

(54) COMPOSITIONS AND METHODS FOR TREATMENT OF HEPATITIS C VIRUS-ASSOCIATED DISEASES

(75) Inventors: Kevin P. Anderson, Carlsbad; Ronnie C. Hanecak, San Clemente, both of CA (US); Chikateru Nozaki, Kumamoto (JP)

(73) Assignee: Isis Pharmaceuticals, Inc., Carlsbad, CA (US)

(*) Notice: Under 35 U.S.C. 154(b), the term of this patent shall be extended for 0 days.

This patent is subject to a terminal disclaimer.

(21) Appl. No.: 08/988,321

(22) Filed: Dec. 10, 1997

Related U.S. Application Data

(63) Continuation-in-part of application No. 08/650,093, filed on May 17, 1996, which is a continuation-in-part of application No. 08/452,841, filed on May 30, 1995, which is a continuation-in-part of application No. 08/397,220, filed on Mar. 9, 1995, which is a continuation-in-part of application No. 07/945,289, filed on Sep. 10, 1992, now abandoned.

(51) Int. Cl.[7] .................... A61K 31/711; A61K 31/7115; A61K 31/7125
(52) U.S. Cl. .......................... 514/44; 536/23.1; 536/24.5
(58) Field of Search .................... 435/6, 91.1, 172.3, 435/325; 514/44; 536/23.1, 24.5, 24.3

(56) References Cited

U.S. PATENT DOCUMENTS

| | | | |
|---|---|---|---|
| 4,806,463 | 2/1989 | Goodchild et al. | 435/5 |
| 5,004,810 | 4/1991 | Draper | 536/24.5 |
| 5,034,506 | 7/1991 | Summerton et al. | 528/391 |
| 5,138,045 | 8/1992 | Cook et al. | 536/24.5 |
| 5,166,195 | 11/1992 | Ecker | 514/44 |
| 5,194,428 | 3/1993 | Agrawal et al. | 514/44 |
| 5,218,105 | 6/1993 | Cook et al. | 236/25.31 |
| 5,264,423 | 11/1993 | Cohen et al. | 514/44 |
| 5,276,019 | 1/1994 | Cohen et al. | 514/44 |
| 5,459,255 | 10/1995 | Cook et al. | 536/27.13 |
| 5,610,054 | 3/1997 | Draper | 435/363 |

FOREIGN PATENT DOCUMENTS

| | | |
|---|---|---|
| 2104649 | 8/1993 | (CA) . |
| 318216 | 11/1988 | (EP) . |
| 419182 | 9/1990 | (EP) . |
| WO 93/24510 | 12/1993 | (WO) . |
| WO 94/08002 | 4/1994 | (WO) . |
| WO 94/24864 | 11/1994 | (WO) . |

OTHER PUBLICATIONS

Choo et al., "Isolation of a cDNA Clone Derived from a Blood–Borne Non–A, Non–B Viral Hepatitis Genome", *Science* 1989, 244, 359–362.

Choo et al., "Genetic organization and diversity of the hepatitis C virus", *Proc. Natl. Acad. Sci.* 1991, 88, 2451–2455.

*BioWorld Today*, Apr. 29, 1994, p. 3.

Egholm et al., "Peptide Nucleic Acids (PNA). Oligonucleotide Analogues with an Achiral Peptide Backbone", *J. Am. Chem. Soc.* 1992, 114, 1895.

Egholm et al., "Recognition of Guanine and Adenine in DNA by Cytosine and Thymine Containing Peptide Nucleic Acids (PNA)", *J. Am. Chem. Soc.* 1992, 114, 9677.

Han et al., "Characterization of the terminal regions of hepatitis C viral RNA: Indentification of conserved sequences in the 5' untranslated region and poly(A) tails at the 3' end," *Proc. Natl. Acad. Sci.* 1991, 88, 1711–1715.

Inchauspe et al., "Genomic structure of the human prototype strain H of hepatitis C virus: Comparison with American and Japanese isolates," *Proc. Natl. Acad. Sci.* 1991, 88, 10292–10296.

Inoue, et al., "Synthesis and hybridization studies on two complementary nona(2'–O–methyl)ribonucleotides," *Nucleic Acids Research* 1991, 15:6131–6148.

Nielsen et al., "Sequence–selective recognition of DNA by strand displacement with a thymine–substituted polyamide," *Science* 1991, 254:1497–1500.

Sproat et al., "New synthetic routes to protected purine 2'–O–methylriboside–3'–O–phosphoramidites using a novel alkylation procedure," *Nucleic Acids Research* 18:41–49 (1990).

Takamizawa et al., "Structure and organization of the hepatitis C virus genome isolated from human carriers," *J. Virol.* 1991, 65:1105–1113.

Tsukiyama–Kohara et al., "Internal ribosome entry site within hepatitis C virus RNA," *J. Virol.* 1992, 66:1476–1483.

Vasseur et al., "Oligonucleosides: Synthesis of a Novel Methylhydroxylamine–Linked Nucleoside Dimer and Its Incorporation into Antisense Sequences", *J. Am. Chem. Soc.* 1992, 114, 4006–4007.

Wakita and Wands, "Specific Inhibition of Hepatitis C Virus Expression by Antisense Oliogdeoxynucleotides", *J. Biol. Chem.* 1994, 269, 14205–14210.

(List continued on next page.)

*Primary Examiner*—David Guzo
(74) *Attorney, Agent, or Firm*—Law Offices of Jane Massey Licata

(57) ABSTRACT

Antisense oligonucleotides are provided which are complementary to and hybridizable with at least a portion of HCV RNA and which are capable of inhibiting the function of the HCV RNA. These oligonucleotides can be administered to inhibit the activity of Hepatitis C virus in vivo or in vitro. These compounds can be used either prophylactically or therapeutically to reduce the severity of diseases associated with Hepatitis C virus, and for diagnosis and detection of HCV and HCV-associated diseases. Methods of using these compounds are also disclosed.

11 Claims, No Drawings

OTHER PUBLICATIONS

Berge et al., "Pharmaceutical Salts," *J. of Pharma Sci.* 1977, 66:1.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets" *J. Med. Chem.* 1993, 36, 831.

De Mesmaeker et al., "Antisense Oligonucleotides", *Acc. Chem. Res.* 1995, 28, 366, Chiang et al., "Antisense Oligonucleotides Inhibit Intercellular Adhesion Molecule 1 Expression by Two Distinct Mechanisms" *J. Biol. Chem.* 1991, 266, 18162.

Martin, "Ein Neuer Zugang zu 2'–O–Alkylribonucleosiden und Eigenschaften deren Oligonucleotide" *Helv. Chim. Acta* 1995, 78, 486–504.

Hanecak et al., "Antisense Oligonucleotide Inhibition of Hepatitis C Virus Gene Expression in Transformed Hepatocytes" *J. Virol.* 1996, 70, 5203–5212.

Dean and Griffey, "Identification and Characterization of Second–Generation Antisense Oligonucleotides" *Antisense and Nucleic Acid Drug Development* 1997, 7.

Henry et al., "Toxicological and pharmacokinetic properties of chemically modified antisense oligonucleotide inhibitors of PKC–α and C–raf kinase" *Anti–Cancer Drug Design* 1997, 12, 409–412.

Branch TIBS 23:45–50 (Feb. 1998).*

* cited by examiner

```
                            SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
          (A) LENGTH: 20
          (B) TYPE: nucleic acid
          (C) STRANDEDNESS: Single
          (D) TOPOLOGY: Linear (iv) ANTI-SENSE: Yes (xi) SEQUENCE DESCRIPTION:  SEQ ID NO: 1:

TGCACGGTCT ACGAGACCTC                                                  20

(2) INFORMATION FOR SEQ ID NO: 2:

(i) SEQUENCE CHARACTERISTICS:
          (A) LENGTH: 20
          (B) TYPE: nucleic acid
          (C) STRANDEDNESS: Single
          (D) TOPOLOGY: Linear (iv) ANTI-SENSE: Yes (xi) SEQUENCE DESCRIPTION:  SEQ ID NO: 2:

GGTGCACGGT CTACGAGACC                                                  20

(2) INFORMATION FOR SEQ ID NO: 3:

(i) SEQUENCE CHARACTERISTICS:
          (A) LENGTH: 20
          (B) TYPE: nucleic acid
          (C) STRANDEDNESS: Single
          (D) TOPOLOGY: Linear (iv) ANTI-SENSE: Yes (xi) SEQUENCE DESCRIPTION:  SEQ ID NO: 3:

ATGGTGCACG GTCTACGAGA                                                  20

(2) INFORMATION FOR SEQ ID NO: 4:

(i) SEQUENCE CHARACTERISTICS:
          (A) LENGTH: 20
          (B) TYPE: nucleic acid
          (C) STRANDEDNESS: Single
          (D) TOPOLOGY: Linear (iv) ANTI-SENSE: Yes (xi) SEQUENCE DESCRIPTION:  SEQ ID NO: 4:

TCATGGTGCA CGGTCTACGA                                                  20

(2) INFORMATION FOR SEQ ID NO: 5:
```

(i) SEQUENCE CHARACTERISTICS:
    (A) LENGTH: 20
    (B) TYPE: nucleic acid
    (C) STRANDEDNESS: Single
    (D) TOPOLOGY: Linear (iv) ANTI-SENSE: Yes (xi) SEQUENCE DESCRIPTION: SEQ ID NO: 5:

GCTCATGGTG CACGGTCTAC                                      20

(2) INFORMATION FOR SEQ ID NO: 6:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 6:

GTGCTCATGG TGCACGGTCT                                      20

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 7:

TCGTGCTCAT GGTGCACGGT                                      20

(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 8:

ATTCGTGCTC ATGGTGCACG                                      20

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 9:

GGATTCGTGC TCATGGTGCA                                      20

(2) INFORMATION FOR SEQ ID NO: 10:

(i) SEQUENCE CHARACTERISTICS:
        (A) LENGTH: 20
        (B) TYPE: nucleic acid (C) STRANDEDNESS: Single
           (D) TOPOLOGY: Linear (iv) ANTI-SENSE: Yes (xi) SEQUENCE DESCRIPTION: SEQ ID NO: 10:

TAGGATTCGT GCTCATGGTG                                              20

(2) INFORMATION FOR SEQ ID NO: 11:

(i) SEQUENCE CHARACTERISTICS:
           (A) LENGTH: 20
           (B) TYPE: nucleic acid
           (C) STRANDEDNESS: Single
           (D) TOPOLOGY: Linear (iv) ANTI-SENSE: Yes (xi) SEQUENCE DESCRIPTION: SEQ ID NO: 11:

TTTAGGATTC GTGCTCATGG                                              20

(2) INFORMATION FOR SEQ ID NO: 12:

(i) SEQUENCE CHARACTERISTICS:
           (A) LENGTH: 20
           (B) TYPE: nucleic acid
           (C) STRANDEDNESS: Single
           (D) TOPOLOGY: Linear (iv) ANTI-SENSE: Yes (xi) SEQUENCE DESCRIPTION: SEQ ID NO: 12:

GGTTTAGGAT TCGTGCTCAT                                              20

(2) INFORMATION FOR SEQ ID NO: 13:

(i) SEQUENCE CHARACTERISTICS:
           (A) LENGTH: 20
           (B) TYPE: nucleic acid
           (C) STRANDEDNESS: Single
           (D) TOPOLOGY: Linear (iv) ANTI-SENSE: Yes (xi) SEQUENCE DESCRIPTION: SEQ ID NO: 13:

GAGGTTTAGG ATTCGTGCTC                                              20

(2) INFORMATION FOR SEQ ID NO: 14:

(i) SEQUENCE CHARACTERISTICS:
           (A) LENGTH: 20
           (B) TYPE: nucleic acid
           (C) STRANDEDNESS: Single
           (D) TOPOLOGY: Linear (iv) ANTI-SENSE: Yes (ix) FEATURE:
           (A) NAME/KEY:
           (B) LOCATION:
           (C) IDENTIFICATION METHOD:
           (D) OTHER INFORMATION:   modified base denoted as N is
               inosine (xi) SEQUENCE DESCRIPTION: SEQ ID NO: 14:

GAGGTTTAGG ATTNGTGCTC                                              20

(2) INFORMATION FOR SEQ ID NO: 15:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (ix) FEATURE:
            (A) NAME/KEY:
            (B) LOCATION:
            (C) IDENTIFICATION METHOD:
            (D) OTHER INFORMATION:   modified base denoted as N is
                inosine (xi) SEQUENCE DESCRIPTION:  SEQ ID NO: 15:

GNGGTTTNGG ATTNGTGCTC                                                            20

(2) INFORMATION FOR SEQ ID NO: 16:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (ix) FEATURE:
            (A) NAME/KEY:
            (B) LOCATION:
            (C) IDENTIFICATION METHOD:
            (D) OTHER INFORMATION:   modified base denoted by N is
                inosine (xi) SEQUENCE DESCRIPTION:  SEQ ID NO: 16:

GNGGTTTNGG ANNNGTGCTC                                                            20

(2) INFORMATION FOR SEQ ID NO: 17:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION:  SEQ ID NO: 17:

TTGAGGTTTA GGATTCGTGC                                                            20

(2) INFORMATION FOR SEQ ID NO: 18:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION:  SEQ ID NO: 18:

CTTTGAGGTT TAGGATTCGT                                                            20

(2) INFORMATION FOR SEQ ID NO: 19:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 19:

TTCTTTGAGG TTTAGGATTC                                                      20

(2) INFORMATION FOR SEQ ID NO: 20:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 20:

TTTTCTTTGA GGTTTAGGAT                                                      20

(2) INFORMATION FOR SEQ ID NO: 21:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 21:

GTTTTCTTT GAGGTTTAGG                                                       20

(2) INFORMATION FOR SEQ ID NO: 22:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 22:

TGGTTTTTCT TTGAGGTTTA                                                      20

(2) INFORMATION FOR SEQ ID NO: 23:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 23:

TTTGGTTTTT CTTTGAGGTT                                                      20

(2) INFORMATION FOR SEQ ID NO: 24:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: Yes (xi) SEQUENCE DESCRIPTION: SEQ ID NO: 24:

```
CGTTTGGTTT TTCTTTGAGG                                                    20
```

(2) INFORMATION FOR SEQ ID NO: 25:

(i) SEQUENCE CHARACTERISTICS:
        (A) LENGTH: 18
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 25:

```
GTGCTCATGG TGCACGGT                                                      18
```

(2) INFORMATION FOR SEQ ID NO: 26:

(i) SEQUENCE CHARACTERISTICS:
        (A) LENGTH: 17
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 26:

```
GTGCTCATGG TGCACGG                                                       17
```

(2) INFORMATION FOR SEQ ID NO: 27:

(i) SEQUENCE CHARACTERISTICS:
        (A) LENGTH: 16
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 27:

```
GTGCTCATGG TGCACG                                                        16
```

(2) INFORMATION FOR SEQ ID NO: 28:

(i) SEQUENCE CHARACTERISTICS:
        (A) LENGTH: 15
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 28:

```
GTGCTCATGG TGCAC                                                         15
```

(2) INFORMATION FOR SEQ ID NO: 29:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 29:

```
GTGCTCATGG                                                               10
```

(2) INFORMATION FOR SEQ ID NO: 30:

(i) SEQUENCE CHARACTERISTICS:
        (A) LENGTH: 18
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 30:

GCTCATGGTG CACGGTCT                                          18

(2) INFORMATION FOR SEQ ID NO: 31:

(i) SEQUENCE CHARACTERISTICS:
        (A) LENGTH: 17
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 31:

CTCATGGTGC ACGGTCT                                           17

(2) INFORMATION FOR SEQ ID NO: 32:

(i) SEQUENCE CHARACTERISTICS:
        (A) LENGTH: 15
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 32:

CATGGTGCAC GGTCT                                              15

(2) INFORMATION FOR SEQ ID NO: 33:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 33:

TGCACGGTCT                                                      10

(2) INFORMATION FOR SEQ ID NO: 34:

(i) SEQUENCE CHARACTERISTICS:
        (A) LENGTH: 18
        (B) TYPE: nucleic acid
        (C) STRANDEDNESS: Single
        (D) TOPOLOGY: Linear (iv) ANTI-SENSE: Yes (xi) SEQUENCE DESCRIPTION: SEQ ID NO: 34:

TGCTCATGGT GCACGGTC                                          18

(2) INFORMATION FOR SEQ ID NO: 35:

(i) SEQUENCE CHARACTERISTICS:
        (A) LENGTH: 16

(B) TYPE: nucleic acid
       (C) STRANDEDNESS: Single
       (D) TOPOLOGY: Linear (iv) ANTI-SENSE: Yes (xi) SEQUENCE DESCRIPTION: SEQ ID NO: 35:

GCTCATGGTG CACGGT                                                          16

(2) INFORMATION FOR SEQ ID NO: 36:

(i) SEQUENCE CHARACTERISTICS:
       (A) LENGTH: 21
       (B) TYPE: nucleic acid
       (C) STRANDEDNESS: Single
       (D) TOPOLOGY: Linear (iv) ANTI-SENSE: Yes (xi) SEQUENCE DESCRIPTION: SEQ ID NO: 36:

GCCGAGGTCC ATGTCGTACG C                                                    21

(2) INFORMATION FOR SEQ ID NO: 37:

(i) SEQUENCE CHARACTERISTICS:
       (A) LENGTH: 686
       (B) TYPE: nucleic acid
       (C) STRANDEDNESS: Single
       (D) TOPOLOGY: Linear (iv) ANTI-SENSE: No (xi) SEQUENCE DESCRIPTION: SEQ ID NO: 37:

GCCAGCCCCC GAUUGGGGGC GACACUCCAC CAUAGAUCAC UCCCCUGUGA                      50

GGAACUACUG UCUUCACGCA GAAAGCGUCU AGCCAUGGCG UUAGUAUGAG                     100

UGUCGUGCAG CCUCCAGGAC CCCCCCUCCC GGGAGAGCCA UAGUGGUCUG                     150

CGGAACCGGU GAGUACACCG GAAUUGCCAG GACGACCGGG UCCUUUCUUG                     200

GAUCAACCCG CUCAAUGCCU GGAGAUUUGG GCGUGCCCCC GCGAGACUGC                     250

UAGCCGAGUA GUGUUGGGUC GCGAAAGGCC UUGUGGUACU GCCUGAUAGG                     300

GUGCUUGCGA GUGCCCCGGG AGGUCUCGUA GACCGUGCAC CAUGAGCACG                     350

AAUCCUAAAC CUCAAAGAAA AACCAAACGU AACACCAACC GCCGCCCACA                     400

GGAGGUCAAG UUCCCGGGCG GUGGUCAGAU CGUUGGUGGA GUUUACCUGU                     450

UGCCGCGCAG GGGCCCCAGG UUGGGUGUGC GCGCGAUCAG GAAGACUUCC                     500

GAGCGGUCGC AACCCCGUGG AAGGCGACAG CCUAUCCCCA AGGCUCGCCG                     550

GCCCGAGGGC AGGGCCUGGG CUCAGCCCGG GUAUCCUUGG CCCCUCUAUG                     600

GCAAUGAGGG CAUGGGGUGG GCAGGAUGGC UCCUGUCACC CCGCGGCUCC                     650

CGGCCUAGUU GGGGCCCCAC GGACCCCCGG CGUAGG                                   686

COMPOSITIONS AND METHODS FOR TREATMENT OF HEPATITIS C VIRUS-ASSOCIATED DISEASES

INTRODUCTION

This application is a continuation-in-part of U.S. Ser. No. 08/650,093, filed May 17, 1996, which is a continuation-in-part of U.S. Ser. No. 08/452,841, filed May 30, 1995, which in turn is a continuation-in-part of U.S. Ser. No. 08/397,220, filed Mar. 9, 1995, which is a continuation-in-part of U.S. Ser. No. 07/945,289, filed Sep. 10, 1992, now abandoned.

FIELD OF THE INVENTION

This invention relates to the design and synthesis of antisense oligonucleotides which can be administered to inhibit the activity of Hepatitis C virus in vivo or in vitro and to prevent or treat Hepatitis C virus-associated disease. These compounds can be used either prophylactically or therapeutically to reduce the severity of diseases associated with Hepatitis C virus. These compounds can also be used for detection of Hepatitis C virus and diagnosis of Hepatitis C virus-associated diseases. Oligonucleotides which are specifically hybridizable with Hepatitis C virus RNA targets and are capable of inhibiting the function of these RNA targets are disclosed. Methods of using these compounds are also disclosed.

BACKGROUND OF THE INVENTION

The predominant form of hepatitis currently resulting from transfusions is not related to the previously characterized Hepatitis A virus or Hepatitis B virus and has, consequently, been referred to as Non-A, Non-B Hepatitis (NANBH). NANBH currently accounts for over 90% of cases of post-transfusion hepatitis. Estimates of the frequency of NANBH in transfusion recipients range from 5%–13% for those receiving volunteer blood, or 25%–54% for those receiving blood from commercial sources.

Acute NANBH, while often less severe than acute disease caused by Hepatitis A or Hepatitis B viruses, can lead to severe or fulminant hepatitis. Of greater concern, progression to chronic hepatitis is much more common after NANBH than after either Hepatitis A or Hepatitis B infection. Chronic NANBH has been reported in 10%–70% of infected individuals. This form of hepatitis can be transmitted even by asymptomatic patients, and frequently progresses to malignant disease such as cirrhosis and hepatocellular carcinoma. Chronic active hepatitis, with or without cirrhosis, is seen in 44%–90% of posttransfusion hepatitis cases. Of those patients who developed cirrhosis, approximately one-fourth died of liver failure.

Chronic active NANBH is a significant problem to hemophiliacs who are dependent on blood products; 5%–11% of hemophiliacs die of chronic end-stage liver disease. Cases of NANBH other than those traceable to blood or blood products are frequently associated with hospital exposure, accidental needle stick, or tattooing. Transmission through close personal contact also occurs, though this is less common for NANBH than for Hepatitis B.

The causative agent of the majority of NANBH has been identified and is now referred to as Hepatitis C Virus (HCV). Houghton et al., EP Publication 318,216; Choo et al., *Science* 1989, 244, 359–362. Based on serological studies using recombinant DNA-generated antigens it is now clear that HCV is the causative agent of most cases of post-transfusion NANBH. The HCV genome is a positive or plus-strand RNA genome. EP Publication 318,216 (Houghton et al.) discloses partial genomic sequences of HCV-1, and teaches recombinant DNA methods of cloning and expressing HCV sequences and HCV polypeptides, techniques of HCV immunodiagnostics, HCV probe diagnostic techniques, anti-HCV antibodies, and methods of isolating new HCV sequences. Houghton et al. also disclose additional HCV sequences and teach application of these sequences and polypeptides in immunodiagnostics, probe diagnostics, anti-HCV antibody production, PCR technology and recombinant DNA technology. The concept of using antisense polynucleotides as inhibitors of viral replication is disclosed, but no specific targets are taught. oligomer probes and primers based on the sequences disclosed are also provided. EP Publication 419,182 (Miyamura et al.) discloses new HCV isolates J1 and J7 and use of sequences distinct from HCV-1 sequences for screens and diagnostics.

The only treatment regimen shown to be effective for the treatment of chronic NANBH is interferon-$\alpha$. Most NANBH patients show an improvement of clinical symptoms during interferon treatment, but relapse is observed in at least half of patients when treatment is interrupted. Long term remissions are achieved in only about 20% of patients even after 6 months of therapy. Significant improvements in antiviral therapy are therefore greatly desired. An obvious need exists for a clinically effective antiviral therapy for acute and chronic HCV infections. Such an antiviral would also be useful for preventing the development of HCV-associated disease, for example for individuals accidently exposed to blood products containing infectious HCV. There is also a need for research reagents and diagnostics which are able to differentiate HCV-derived hepatitis from hepatitis caused by other agents and which are therefore useful in designing appropriate therapeutic regimes.

Antisense Oligonucleotides

Oligonucleotides are commonly used as research reagents and diagnostics. For example, antisense oligonucleotides, which, by nature, are able to inhibit gene expression with exquisite specificity, are often used by those of ordinary skill to elucidate the function of particular genes, for example to determine which viral genes are essential for replication, or to distinguish between the functions of various members of a biological pathway. This specific inhibitory effect has, therefore, been exploited for research use. This specificity and sensitivity is also harnessed by those of skill in the art for diagnostic uses. Viruses capable of causing similar hepatic symptoms can be easily and readily distinguished in patient samples, allowing proper treatment to be implemented. Antisense oligonucleotide inhibition of viral activity in vitro is useful as a means to determine a proper course of therapeutic treatment. For example, before a patient suspected of having an HCV infection is contacted with an oligonucleotide composition of the present invention, cells, tissues or a bodily fluid from the patient can be contacted with the oligonucleotide and inhibition of viral RNA function can be assayed. Effective in vitro inhibition of HCV RNA function, routinely assayable by methods such as Northern blot or RT-PCR to measure RNA replication, or Western blot or ELISA to measure protein translation, indicates that the infection will be responsive to the oligonucleotide treatment.

Oligonucleotides have also been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. As examples, U.S. Pat. No. 5,166,195 issued Nov. 24, 1992, provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely and effectively administered to humans and clinical trials of several antisense oligonucleotide drugs are presently underway. The phosphorothioate oligonucleotide, ISIS 2922, has been shown to be effective against cytomegalovirus retinitis in AIDS patients. *BioWorld Today*, Apr. 29, 1994, p. 3. It is thus established that oligonucleotides can be useful drugs for treatment of cells and animal subjects, especially humans.

Seki et al. have disclosed antisense compounds complementary to specific defined regions of the HCV genome. Canadian patent application 2,104,649.

Hang et al. have disclosed antisense oligonucleotides complementary to the 5' untranslated region of HCV for controlling translation of HCV proteins, and methods of using them. WO 94/08002.

Blum et al. have disclosed antisense oligonucleotides complementary to an RNA complementary to a portion of a hepatitis viral genome which encodes the terminal protein region of the viral polymerase, and methods of inhibiting replication of a hepatitis virus using such oligonucleotides. WO 94/24864.

Wakita and Wands have used sense and antisense oligonucleotides to determine the role of the 5' end untranslated region in the life cycle of HCV. Antisense oligonucleotides targeted to three regions of the 5' untranslated region and one region of the core protein coding region effectively blocked in vitro translation of HCV protein, suggesting that these domains may be critical for HCV translation. *J. Biol. Chem.* 1994, 269, 14205–14210.

SUMMARY OF THE INVENTION

In accordance with the present invention, compositions and methods for modulating the effects of HCV infection are provided. Oligonucleotides which are complementary to, and specifically hybridizable with, selected sequences of HCV RNA and which are capable of inhibiting the function of the HCV RNA are provided. The HCV polyprotein translation initiation codon region is a preferred target. An oligonucleotide (SEQ ID NO: 6) targeted to nucleotides 330–349 of the initiation codon region is particularly preferred, and this sequence comprising a 5-methylcytidine at every cytidine residue is even more preferred. Methods for diagnosing or treating disease states by administering oligonucleotides, either alone or in combination with a pharmaceutically acceptable carrier, to animals suspected of having HCV-associated diseases are also provided.

DETAILED DESCRIPTION OF THE INVENTION

Several regions of the HCV genome have been identified as antisense targets in the present invention. The size of the HCV genome is approximately 9400 nucleotides, with a single translational reading frame encoding a polyprotein which is subsequently processed to several structural and non-structural proteins. It should be noted that sequence availability and nucleotide numbering schemes vary from strain to strain. The 5' untranslated region (5' UTR) or 5' noncoding region (5' NCR) of HCV consists of approximately 341 nucleotides upstream of the polyprotein translation initiation codon. A hairpin loop present at nucleotides 1–22 at the 5' end of the genome (HCV-1) identified herein as the "5' end hairpin loop" is believed to serve as a recognition signal for the viral replicase or nucleocapsid proteins. Han et al., *Proc. Natl. Acad. Sci.* 1991, 88, 1711–1715. The 5' untranslated region is believed to have a secondary structure which includes six stem-loop structures, designated loops A–F. Loop A is present at approximately nucleotides 13–50, loop B at approximately nucleotides 51–88, loop C at approximately nucleotides 100–120, loop D at approximately nucleotides 147–162, loop E at approximately nucleotides 163–217, and loop F at approximately nucleotides 218–307. Tsukiyama-Kohara et al., *J. Virol.* 1992, 66, 1476–1483. These structures are well conserved between the two major HCV groups.

Three small (12–16 amino acids each) open reading frames (ORFs) are located in the 5'-untranslated region of HCV RNA. These ORFs may be involved in control of translation. The ORF 3 translation initiation codon as denominated herein is found at nucleotides 315–317 of HCV-1 according to the scheme of Han et al., *Proc. Natl. Acad. Sci.* 1991, 88, 1711–1715; and at nucleotides −127 to −125 according to the scheme of Choo et al., *Proc. Natl. Acad. Sci.* 1991, 88, 2451–2455.

The polyprotein translation initiation codon as denominated herein is an AUG sequence located at nucleotides 342–344 of HCV-1 according to Han et al., *Proc. Natl. Acad. Sci.* 1991, 88, 1711–1715 or at nucleotide 1–3 according to the HCV-1 numbering scheme of Choo et al., *Proc. Natl. Acad. Sci.* 1991, 88, 2451–2455. Extending downstream (toward 3' end) from the polyprotein AUG is the core protein coding region.

The 3' untranslated region, as denominated herein, consists of nucleotides downstream of the polyprotein translation termination site (ending at nt 9037 according to Choo et al.; nt 9377 according to schemes of Han and Inchauspe). Nucleotides 9697–9716 (numbering scheme of Inchauspe for HCV-H) at the 3' terminus of the genome within the 3' untranslated region can be organized into a stable hairpin loop structure identified herein as the 3' hairpin loop. A short nucleotide stretch (R2) immediately upstream (nt 9691–9696 of HCV-H) of the 3' hairpin, and denominated herein "the R2 sequence", is thought to play a role in cyclization of the viral RNA, possibly in combination with a set of 5' end 6-base-pair repeats of the same sequence at nt 23–28 and 38–43. (Inchauspe et al., *Proc. Natl. Acad. Sci.* 1991, 88, 10292–10296) is identified herein as "5' end 6-base-pair repeat". Palindrome sequences present near the 3' end of the genome (nucleotides 9312–9342 according to the scheme of Takamizawa et al., *J. Virol.* 1991, 65, 1105–1113) are capable of forming a stable secondary structure. This is referred to herein as the 3' end palindrome region.

Antisense Oligonucleotides

The present invention employs oligonucleotides 5 to 50 nucleotides in length which are specifically hybridizable with hepatitis C virus RNA and are capable of inhibiting the function of the HCV RNA. In preferred embodiments, oligonucleotides are targeted to the 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence and 3' end hairpin loop region of HCV RNA. This relationship between an oligonucleotide and the nucleic acid sequence to which it is targeted is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid (RNA or DNA) from an infectious agent. In the present invention, the target is the 5' end hairpin loop, 5' end 6-base-pair repeats, ORF 3 translation initiation codon (all of which are contained within the 5' UTR), polyprotein translation initiation codon, core protein coding region (both of which are contained within the coding region), 3' end palindrome region, R2 sequence or 3' end hairpin loop (all of which are contained within the 3' UTR) of HCV RNA. The targeting process also includes determination of a site or sites within the nucleic acid sequence for the oligonucleotide interaction to occur such that the desired effect, i.e., inhibition of HCV RNA function, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of HCV RNA function is presently the preferred form of modulation in the present invention. The oligonucleotides are able to inhibit the function of viral RNA by interfering with its replication, transcription into mRNA, translation into protein, packaging into viral particles or any other activity necessary to its overall biological function. The failure of the RNA to perform all or part of its function results in failure of all or a portion of the normal life cycle of the virus. This inhibition can be measured, in samples derived from either in vitro or in vivo (animal) systems, in ways which are routine in the art, for example by RT-PCR or Northern blot assay of HCV RNA levels or by in vitro translation, Western blot or ELISA assay of protein expression as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A number of modifications have also been shown to increase binding (affinity) of the oligonucleotide to its target. Affinity of an oligonucleotide for its target is routinely determined by measuring the Tm of an oligonucleotide/target pair, which is the temperature at which the oligonucleotide and target dissociate. Dissociation is detected spectrophotometrically. The higher the Tm, the greater the affinity of the oligonucleotide for the target. In some cases, oligonucleotide modifications which enhance target binding affinity are also, independently, able to enhance nuclease resistance.

Specific examples of some preferred oligonucleotides envisioned for this invention may contain phosphorothioates (P=S), phosphotriesters, methyl phosphonates, short chain alkyl or cycloalkyl intersugar linkages or short chain heteroatomic or heterocyclic intersugar ("backbone") linkages at one or more positions instead of the native phosphodiester (P=O) backbone. Most preferred are phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$) —$CH_2$, $CH_2$—N($CH_3$) —N($CH_3$) —$CH_2$ and O—N($CH_3$)—$CH_2$—$CH_2$ backbones (where phosphodiester is O'P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Oligonucleotides containing one or more PNA, MMI or P=S backbone linkages are presently more preferred. Other preferred oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N—alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a reporter group; an intercalator; a group for improving the pharmacokinetic properties of an oligonucleotide; or a group for improving the pharmacodynamic properties of an oligonucleotide and other substituents having similar properties. Presently preferred modifications include 2'-methoxyethoxy (2'—O—CH$_2$CH$_2$OCH$_3$), 2'-methoxy (2'—O—CH$_3$), 2'—propoxy (2'—OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases known in the art include nucleobases found only infrequently or transiently in natural nucleic acids, e.g., hypoxanthine (whose corresponding nucleotide, inosine, is sometimes referred to as a "universal base"), 6-methyladenine, 5-methylcytosine, 5-hydroxymethylcytosine (HMC), glycosyl HMC and gentiobiosyl HMC, as well synthetic nucleobases, e.g., 5-bromouracil, 5-hydroxymethyluracil, 8-azaguanine, 7-deazaguanine, N$^6$(6-aminohexyl)adenine and 2,6-diaminopurine. Oligonucleotides in which cytosine bases are replaced by 5-methylcytosines are presently a preferred embodiment of the invention.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention. Such lipophilic moieties known in the art include but are not limited to one or more cholesteryl moieties, cholic acids, thioethers, thiocholesterols, aliphatic chains, e.g., dodecandiol or undecyl residues, phospholipids, polyamines or polyethylene glycol chains, adamantane acetic acid, palmityl moieties, octadecylamine or hexylamino-carbonyl-oxycholesterol moiety. Oligonucleotides comprising lipophilic moieties, and methods for preparing such oligonucleotides, as disclosed in U.S. Pat. Nos. 5,138,045, No. 5,218,105 and No. 5,459,255, the contents of which are hereby incorporated by reference.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding HCV RNA) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase HCV RNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of HCV RNA function. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance. oligonucleotides which contain at least one phosphorothioate modification are presently more preferred.

The compounds of the present invention include bioequivalent compounds, including pharmaceutically acceptable salts and prodrugs.

The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

Pharmaceutically acceptable salts are physiologically and pharmaceutically acceptable salts of the nucleic acids of the invention ,i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.* 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as inorganic acids, for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid.

Pharmaceutically acceptable salts of compounds may also be formed with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a prodrug form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

The oligonucleotides in accordance with this invention preferably are from about 5 to about 50 nucleotides in length. In the context of this invention it is understood that this encompasses non-naturally occurring oligomers as hereinbefore described, having 5 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as those available from Glen Research, Sterling Va., to synthe-size modified oligonucleotides such as cholesterol-modified oligonucleotides.

Methods of modulating the activity of HCV virus are provided, in which the virus, or cells, tissues or bodily fluid suspected of containing the virus, is contacted with an oligonucleotide of the invention. In the context of this invention, to "contact" means to add the oligonucleotide to a preparation of the virus, or vice versa, or to add the oligonucleotide to a preparation or isolate of cells, tissues or bodily fluid, or vice versa, or to add the oligonucleotide to virus, cells tissues or bodily fluid in situ, i.e., in an animal, especially a human.

The oligonucleotides of this invention can be used in diagnostics, therapeutics and as research reagents and kits. Since the oligonucleotides of this invention hybridize to RNA from HCV, sandwich and other assays can easily be constructed to exploit this fact. Provision of means for detecting hybridization of oligonucleotide with HCV or HCV RNA present in a sample suspected of containing it can routinely be accomplished. Such provision may include enzyme conjugation, radiolabelling or any other suitable detection systems. Kits for detecting the presence or absence of HCV may also be prepared. The specific ability of the oligonucleotides of the invention to inhibit HCV RNA function can also be exploited in the detection and diagnosis of HCV, HCV infection and HCV-associated diseases. As described in the examples of the present application, the decrease in HCV RNA or protein levels as a result of oligonucleotide inhibition of HCV RNA function can be routinely detected, for example by RT-PCR, Northern blot, Western blot or ELISA.

For prophylactics and therapeutics, methods of preventing HCV-associated disease and of treating HCV infection and HCV-associated disease are provided. The formulation of therapeutic compositions and their subsequent administration is believed to be within the skill in the art. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives.

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. For oral administration, it has been found that oligonucleotides with at least one 2'-substituted ribonucleotide are particularly useful because of their absorption and distribution characteristics. U.S. Pat. No. 5,591,721 issued to Agrawal et al. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives.

Dosing is dependent on severity and responsiveness of the condition to be treated, with course of treatment lasting from several days to several months or until a reduction in viral titer (routinely measured by Western blot, ELISA, RT-PCR, or RNA (Northern) blot, for example) is effected or a diminution of disease state is achieved. Optimal dosing schedules are easily calculated from measurements of drug accumulation in the body. Persons of ordinary skill can easily determine optimum dosages, dosing methodologies and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of drug compound (derived from oligonucleotide sequence and chemical structure) and an experimentally derived effective dose such as an $IC_{50}$, for example, a dose in mg/kg is routinely calculated. In general, dosage is from 0.001 µg to 100 g and may be administered once or several times daily, weekly, monthly or yearly, or even every 2 to 20 years.

Pharmacokinetics of Antisense Oligonucleotides

Because the primary pathology associated with HCV infection occurs in the liver of infected individuals, the ability of a potential anti-HCV compound to achieve significant concentrations in the liver is advantageous. Pharmacokinetic profiles for a number of oligonucleotides, primarily phosphorothioate oligonucleotides, have been determined. Phosphorothioate oligonucleotides have been shown to have very similar pharmacokinetics and tissue distribution, regardless of sequence. This is characterized in plasma by a rapid distribution phase (approximately 30 minutes) and a prolonged elimination phase (approximately 40 hours). Phosphorothioates are found to be broadly distributed to peripheral tissues (i.e., excepting the brain, which is reachable directly, e.g., by intraventricular drug administration, and in addition may be reachable via a compromised blood-brain barrier in many nervous system conditions), with the highest concentrations found in liver, renal cortex and bone marrow. There is good accumulation of intact compound in most tissues, particularly liver, kidney and bone marrow, with very extended compound half-life in tissues. Similar distribution profiles are found whether the oligonucleotide is administered intravenously or subcutaneously. Furthermore, the pharmacokinetic and tissue distribution profiles are very consistent among animal species, including rodents, monkeys and humans.

Preferred Embodiments of the Invention

It has been found that antisense oligonucleotides designed to target viruses can be effective in diminishing viral infection.

In accordance with this invention, persons of ordinary skill in the art will understand that messenger RNA includes not only the sequence information to encode a protein using the three letter genetic code, but also associated ribonucleotides which form regions known to such persons as the 5'-untranslated region, the 3'-untranslated region, and the 5' cap region, as well as ribonucleotides which form various secondary structures. Thus, oligonucleotides may be formulated in accordance with this invention which are targeted wholly or in part to these associated ribonucleotides as well as to the coding ribonucleotides. In preferred embodiments, the oligonucleotide is specifically hybridizable with the HCV 5' end hairpin loop, 5' end 6-base-pair repeats, ORF 3 translation initiation codon, (all of which are contained within the 5' UTR) polyprotein translation initiation codon, core protein coding region (both of which are contained within the coding region) , R2 region, 3' hairpin loop or 3' end palindrome region (all of which are contained within the 3'-untranslated region).

It is to be expected that differences in the RNA of HCV from different strains and from different types within a strain exist. It is believed that the regions of the various HCV strains serve essentially the same function for the respective strains and that interference with homologous or analogous RNA regions will afford similar results in the various strains. This is believed to be so even though differences in the nucleotide sequences among the strains exist.

Accordingly, nucleotide sequences set forth in the present specification will be understood to be representational for the particular strain being described. Homologous or analogous sequences for different strains of HCV are specifically contemplated as being within the scope of this invention. In preferred embodiments of the present invention, antisense oligonucleotides are targeted to the 5' untranslated region, core protein translation initiation codon region, core protein coding region, ORF 3 translation initiation codon and 3'-untranslated region of HCV RNA.

In preferred embodiments, the antisense oligonucleotides are hybridizable with at least a portion of the polyprotein translation initiation codon or with at least a portion of the core protein coding region. The sequence of nucleotides 1–686 (SEQ ID NO: 37) comprises the entire 5'-untranslated region (nucleotides 1–341) and a 145-nucleotide core region sequence of HCV RNA. A highly preferred oligonucleotide hybridizable with at least a portion of the polyprotein translation initiation codon comprises SEQ ID NO: 6.

In vitro Evaluation of HCV Antisense Oligonucleotides

HCV replication in cell culture has not yet been achieved. Consequently, in vitro translation assays are used to evaluate antisense oligonucleotides for anti-HCV activity. One such in vitro translation assay was used to evaluate oligonucleotide compounds for the ability to inhibit synthesis of HCV 5' UTR-core-env transcript in a rabbit reticulocyte assay.

Cell-based assays are also used for evaluation of oligonucleotides for anti-HCV activity. In one such assay, effects of oligonucleotides on HCV RNA function are evaluated by measuring RNA and/or HCV core protein levels in transformed hepatocytes expressing the 5'end of the HCV genome. Recombinant HCV/vaccinia virus assays can also be used, such as those described in the examples of the present application. Luciferase assays can be used, for example, as described in the examples of the present application, in which recombinant vaccinia virus containing HCV sequences fused to luciferase sequences are used. Quantitation of luciferase with a luminometer is a simple way of measuring HCV core protein expression and its inhibition by antisense compounds. This can be done in cultured hepatocytes or in tissue samples, such as liver biopsies, from treated animals.

Animal Models for HCV

There is no small animal model for chronic HCV infection. A recombinant vaccinia/HCV/luciferase virus expression assay has been developed for testing compounds in mice. Mice are inoculated with recombinant vaccinia virus (either expressing HCV/luciferase or luciferase alone for a control). Organs (particularly liver) are harvested one or more days later and luciferase activity in the tissue is assayed by luminometry.

The following specific examples are provided for illustrative purposes only and are not intended to limit the invention.

EXAMPLES

Example 1

Oligonucleotide Synthesis

Unmodified oligodeoxynucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.* 1993, 36, 831. Briefly, the protectednucleoside $N^6$-benzoyl-2'-deoxy-2'-fluoroadenosine was synthesized utilizing commercially available 9-8-D-arabinofuranosyladenine as starting material and by modifying literature procedures whereby the 2'-"-fluoro atom is introduced by a $S_N2$-displacement of a 2'-8-O-trifyl group. Thus $N^6$-benzoyl-9-8-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-8-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2, 2'-anhydro-1-8-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

Oligonucleotides having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.* 1995, 28, 366. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science* 1991, 254, 1497).

After cleavage from the controlled pore glass column (Applied Biosystems) and deblocking in concentrated ammonium hydroxide at 55EC for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162. Results obtained with HPLC-purified material were similar to those obtained with non-HPLC purified material.

Oligonucleotides having 2'—O—$CH_2CH_2OCH_3$ modified nucleotides were synthesized according to the method of Martin. *Helv. Chim. Acta* 1995, 78, 486–504. All 2'—O—$CH_2CH_2OCH_3$ cytosines were 5-methyl cytosines, synthesized as follows:

Monomers

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL) The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57w).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHC_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% Et₃NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methylcytidine DMT β-cyanoethyl phosphoramidites are commercially available from PerSeptive Biosystems (Framingham, Mass.).

Example 2

Evaluation of Inhibitory Activity of Antisense oligonucleotides which are targeted to the polyprotein translation initiation codon region and adjacent core protein coding region (1) In order to evaluate the inhibitory activity of antisense oligonucleotides which are complementary to the region including the translation initiation codon (nucleotide number 342–344) of HCV-RNA and the adjacent core protein coding region, a series of 20 mer antisense oligonucleotides were prepared which are complementary to the region from nucleotide 320 to nucleotide 379. These are named according to their target sequence on the HCV RNA, i.e., the oligonucleotide name (e.g., 330) is the number of the 5'-most nucleotide of the corresponding HCV RNA target sequence shown in SEQ ID NO: 37. Accordingly, oligonucleotide 330 is targeted to nucleotides 330–349 of the HCV RNA shown in SEQ ID NO: 37. Of these oligonucleotides, oligonucleotides 324 through 344 contain all or part of the sequence CAT which is complementary to the AUG initiation codon itself. The nucleotide sequence of these antisense oligonucleotides are shown in Table 1.

TABLE 1

Antisense oligonucleotides to HCV

| Oligo | Sequence | % Inhibition | SEQ ID NO: |
|---|---|---|---|
| 320 | TGC ACG GTC TAC GAG ACC TC | 3 | 1 |
| 322 | GGT GCA CGG TCT ACG AGA CC | 5 | 2 |
| 324 | ATG GTG CAC GGT CTA CGA GA | 31 | 3 |
| 326 | TCA TGG TGC ACG GTC TAC GA | 39 | 4 |
| 328 | GCT CAT GGT GCA CGG TCT AC | 71 | 5 |
| 330 | GTG CTC ATG GTG CAC GGT CT | 38 | 6 |
| 332 | TCG TGC TCA TGG TGC ACG GT | 5 | 7 |

TABLE 1-continued

Antisense oligonucleotides to HCV

| Oligo | Sequence | % Inhibition | SEQ ID NO: |
|---|---|---|---|
| 334 | ATT CGT GCT CAT GGT GCA CG | 39 | 8 |
| 336 | GGA TTC GTG CTC ATG GTG CA | 98 | 9 |
| 338 | TAG GAT TCG TGC TCA TGG TG | 99 | 10 |
| 340 | TTT AGG ATT CGT GCT CAT GG | 97 | 11 |
| 342 | GGT TTA GGA TTC GTG CTC AT | 96 | 12 |
| 344 | GAG GTT TAG GAT TCG TGC TC | 99 | 13 |
| 344-i1 | GAG GTT TAG GAT TIG TGC TC | 95 | 14 |
| 344-i3 | GIG GTT TIG GAT TIG TGC TC | 90 | 15 |
| 344-i5 | GIG GTT TIG GAI JIG TGC TC | 51 | 16 |
| 346 | TTG AGG TTT AGG ATT CGT GC | 98 | 17 |
| 348 | CTT TGA GGT TTA GGA TTC GT | 98 | 18 |
| 350 | TTC TTT GAG GTT TAG GAT TC | 99 | 19 |
| 352 | TTT TCT TTG AGG TTT AGG AT | 99 | 20 |
| 354 | GTT TTT CTT TGA GGT TTA GG | 91 | 21 |
| 356 | TGG TTT TTC TTT GAG GTT TA | 86 | 22 |
| 358 | TTT GGT TTT TCT TTG AGG TT | 83 | 23 |
| 360 | CGT TTG GTT TTT CTT TGA GG | 81 | 24 |

The inhibitory activity of these 21 antisense oligonucleotides was evaluated in the in vitro translation assay. As shown in Table 1, antisense oligonucleotides 328, 336, 338, 340, 342, 344, 346, 348, 350, 352, 354, 356, 358 and 360 showed an inhibitory activity of greater than 70%, and are preferred. Of these, 336, 338, 340, 342, 344, 346, 348, 350 and 352 showed an extremely high inhibitory activity of over 95% and are most preferred.

The HCV target sequence regions complementary to the above 9 most active antisense oligonucleotides have in common the four nucleotides from number 352 to 355 in the core protein coding region near the polyprotein translation initiation codon. Thus, it is preferred to target these four nucleotides in order to inhibit the translation. Accordingly, oligonucleotides comprising the sequence GGAT are preferred embodiments of the invention.

(2) Evaluation of antisense oligonucleotides in which the nucleotides known to be variable among strains were replaced by inosine:

It is known that in the nucleotide sequences in the core protein coding region near the translation initiation codon, variation of bases among strains occasionally occurs at nucleotides 350, 351, 352, 356 and 362. Based on this knowledge, it was studied whether substitution of these bases by the "universal base" inosine would be effective for inhibition of various viruses.

An antisense DNA, designated oligonucleotide 344-il, was prepared in which the base at base number 350 in oligonucleotide 344 was replaced by inosine. Likewise, an antisense DNA, designated oligonucleotide 344-i3, in which three bases at base numbers 350, 356 and 362 were substituted by inosine, and an antisense DNA, designated oligonucleotide 344-i5, in which five bases at base numbers 350, 351, 352, 356, and 362 were substituted by inosine, were prepared. The inhibitory activity of these antisense oligonucleotides was evaluated in the in vitro translation assay. As a result, oligonucleotides 344-il and 344-i3 showed high inhibitory activity. Therefore, antisense oligonucleotides targeted to nucleotides 344-363 of HCV RNA and which have three inosine substituents or less are preferred. Their inhibitory activities are shown in Table 1.

Example 3

Evaluation of Oligonucleotides 120, 330 and 340 and truncated versions of oligonucleotides 120, 260, 330 and 340 in H8Ad17 cell assay for effects on HCV RNA levels The anti-HCV activity of P=S oligonucleotides 120, 330 and 340 was evaluated in H8Ad17 cells as follows.

An expression plasmid containing a gene (1.3 kb) coding for 5' NCR-core-env region of HCV gene was prepared by conventional methods and transfected into a liver cell strain (H8Ad17) by lipofection according to standard methods. The desired liver cell transformant, which expressed HCV core protein, was obtained.

HCV RNA was isolated and quantitated by Northern blot analysis to determine levels of expression. Core protein expression could also be detected by ELISA method using an anti-HCV core-mouse monoclonal antibody as the solid phase antibody; an anti-HCV human polyclonal antibody as the primary antibody; and an HRP (horseradish peroxidase)-conjugated anti-human IgG-mouse monoclonal antibody as the secondary antibody.

The liver cell transformant ($2.5 \times 10^5$ cells) were inoculated on 6-well plates. To each plate was added each of the above-obtained five antisense oligonucleotides (each at a concentration of 5 $\mu$M). After two days, the cells were harvested and counted. The cells were washed once and lysed, and the inhibitory activity was measured by Northern blot. The inhibitory activities of the P=S antisense oligonucleotides were calculated, compared to control without antisense oligonucleotide.

As before, the oligonucleotide number is the number of the 5'-most nucleotide of the corresponding HCV RNA target sequence shown in SEQ ID NO: 37. For example, oligonucleotide 120 is a 20 mer targeted to nucleotides 120–139 of HCV RNA. Each of these compounds induced reduction in HCV RNA levels at doses of 0.5 $\mu$M and 0.17 $\mu$M. These three compounds (P=S 20 mers 120, 330 and 340) are therefore highly preferred. 15 mer versions (truncated at by 5 nucleotides at either the 3' or 5' end) induced a reduction of HCV RNA at the 0.5 $\mu$M dose. These compounds are therefore preferred. 10 mers did not show sequence-specific inhibition at either dose.

A number of shortened analogs of oligonucleotide 330 were also synthesized as phosphorothioates and evaluated for effects on HCV RNA levels in the same manner. The sequence of oligonucleotide 330 was truncated at one or both ends. These oligonucleotides are shown in Table 2. Oligonucleotide concentration was 100 nM.

TABLE 2

| Oligo | Sequence | Activity % control | SEQ ID NO |
|---|---|---|---|
| 330 | GTG CTC ATG GTG CAC GGT CT | 30% | 6 |
| 9559 | GTG CTC ATG GTG CAC GGT | 53 | 25 |
| 9557 | GTG CTC ATG GTG CAC GG | 52 | 26 |
| 9558 | GTG CTC ATG GTG CAC G | 66 | 27 |
| 9036 | GTG CTC ATG GTG CAC | 37 | 28 |
| 9035 | GTG CTC ATG G | 100 | 29 |
| 10471 | G CTC ATG GTG CAC GGT CT | 27 | 30 |
| 10470 | CTC ATG GTG CAC GGT CT | 35 | 31 |
| 9038 | C ATG GTG CAC GGT CT | 32 | 32 |
| 9034 | TG CAC GGT CT | 82 | 33 |

TABLE 2-continued

| Oligo | Sequence | Activity % control | SEQ ID NO |
|---|---|---|---|
| 10549 | TG CTC ATG GTG CAC GGT C | 17 | 34 |
| 10550 | G CTC ATG GTG CAC GGT | 36 | 35 |

In this assay, oligonucleotides 9036, 10471, 10470, 9038, 10549 and 10550 gave greater than 50% inhibition of HCV RNA ion and are therefore preferred.

Example 4

Evaluation of oligos 259, 260 and 330 in the HCV H8Ad17 RNA assay

The anti-HCV activity of P=S and 2'-O-propyl/P=S gapped oligonucleotides was evaluated in H8Ad17 cells as described in Example 3. P=S oligonucleotides 259, 260 and 330 all induced similar (approx 55%) reduction in HCV RNA levels in this assay, using 70 nM oligonucleotide concentration. The 2'-O-propyl gapped version of oligonucleotide 259 showed approximately 25% inhibition of HCV RNA levels (170 nM oligo dose), but oligonucleotides 260 and 330 were not active as 2'-O-propyl gapped oligonucleotides in this assay. In a previous assay of the same type, the gapped 2'-O-propyl version of oligonucleotide 330 did induce a reduction of HCV RNA, though less than was observed for the P=S 330 oligonucleotide.

Example 5

Evaluation of oligos 259, 260 and 330 in an HCV H8Ad17 protein assay

A Western blot assay employing affinity-purified human polyclonal anti-HCV serum and $^{125}$I-conjugated goat anti-human IgG was developed in place of ELISA assays previously used to evaluate effects of oligonucleotides on HCV core protein levels. Six-well plates were seeded with H8 cells at $3.5 \times 10^5$ cells/well. Cells were grown overnight. Cells were treated with oligonucleotide in Optimem containing 5 $\mu$g/ml lipofectin for 4 hours. Cells were fed with 2 ml H8 medium and allowed to recover overnight. To harvest cells, cells were washed once with 2 ml PBS, lysed in 100 $\mu$l Laemmli buffer and harvested by scraping. For electrophoresis, cell lysates were boiled, and 10–14 Al of cell lysate was loaded on each lane of a 16% polyacrylamide gel. After electrophoresing, proteins were transferred electrophoretically onto PVDF membrane. The membrane was blocked in PBS containing 2% goat serum and 0.3% TWEEN-20, and incubated overnight with primary antibody (human anti-core antibody 2243 and rabbit anti-G3PDH antibody). The membrane was washed 5×5 minutes in buffer, then incubated with secondary antibodies for 4–8 hours ($^{125}$I-conjugated goat anti-human, and $^{125}$I-conjugated goat anti-rabbit) . The membrane was washed 5×5 minutes in buffer, sealed in plastic and exposed in a PhosphorImager cassette overnight. Bands were quantitated on the PhosphorImager (Molecular Dynamics, Sunnyvale Calif.), normalized to G3PDH expression levels, and results were plotted as a percentage of control untreated cells.

P=S and 2'-modified 330 oligonucleotides were evaluated using this Western blot assay. These oligonucleotides are shown in Table 3. In the sequences shown, capital letters represent base sequence, small letters (o or s) represent internucleoside linkage, either phosphodiester (P=O) or phosphorothioate (P=S), respectively. Bold=2'-O-propyl. *=2'-O-butylimidazole. +=2'-O-propylamine.

TABLE 3

| Oligo # | Sequence | SEQ ID NO |
|---|---|---|
| 330 | GsTsGsCsTsCsAsTsGsGsTsGsCsAsCsGsGsTsCsT | 6 |
| 330 | GsTsGsCsTsCsAsTsGsGsTsGsCsAsCsGsGsTsCsT | 6 |
| 330 | \* \* <br> GsTsGsCsTsCsAsTsGsGsTsGsCsAsCsGsGsTsCsT <br> \* \* | 6 |
| 330 | + + <br> GsTsGsCsTsCsAsTsGsGsTsGsCsAsCsGsGsTsCsT <br> + + | 6 |

Cells were treated with oligonucleotide at doses of 25 nM, 100 nM or 400 nM. The greatest reduction in core protein (approx 90–95% at higher doses) was observed with the P=S oligonucleotide. This compound is therefore highly preferred. The 2'-O-propyl gapped P=S oligonucleotide gave approximately 80% inhibition of core protein expression. This compound is therefore preferred. The 2'-O-propyl/P=O compound did not show activity in this assay.

Example 6

Evaluation of modified 330 oligos in cellular assays

Oligonucleotides with the 330 sequence (SEQ ID NO: 6) and containing various modifications [P=S deoxy; 2'-O-propyl (uniform 2'-O-propyl or 2'-O-propyl gapped, both uniformly P=S); or 2'-fluoro modifications (gapped or uniform, both uniformly P=S)] were evaluated in the H8Ad17 core protein Western blot assay compared to a scrambled phosphorothioate control.

In this assay, the P=S oligonucleotide was consistently the best, giving an average of 62.4% inhibition of HCV core protein translation (n=7) compared to control. 2'-O-propyl and 2'-fluoro gapped oligonucleotides gave over 50% inhibition in at least one experiment. Uniformly 2'-fluoro or uniformly 2'-O-propyl oligonucleotides were inactive in this experiment.

In this assay, the P=S oligonucleotides were consistently the best and are preferred. Of these, P=S oligonucleotides 260, 270, 275, 277 and 330 are more preferred. Uniform 2'fluoro P=S oligonucleotides 345, 347 and 355 are also more preferred.

Additional uniform 2'-fluoro phosphorothioate oligonucleotides were synthesized and tested for ability to inhibit HCV core protein expression. oligonucleotide 344 was also found to be extremely active and is preferred. The region of the HCV RNA target from nucleotide 344 to nucleotide 374 was found to be extremely sensitive to antisense oligonucleotide inhibition. Oligonucleotides complementary to this target region, therefore, are preferred. More preferred among these are the 2'fluoro phosphorothioate oligonucleotides.

Example 7

Evaluation of a "single virus" recombinant vaccinia/HCV core protein assay

A "single virus" vaccinia assay system was developed, which does not require co-infection with helper vaccinia virus expressing T7 polymerase. Cells were pretreated with oligonucleotide in the absence of lipofectin prior to infection with recombinant vaccinia virus expressing HCV sequences. Cells were then infected with recombinant vaccinia virus expressing HCV 5' UTR-core at a m.o.i. of 2.0 pfu/cell. After infection, cells were rinsed and post-treated with medium containing oligonucleotide. Initial results obtained with this assay indicate that P=S oligonucleotides 259 and 260 inhibit HCV 5'-UTR core expression by >60% at a concentration of 1 μM. Inhibition is dose-dependent.

Uniformly 2'-fluoro P=S oligonucleotides 260, 330 and 340 were evaluated for activity in the recombinant vaccinia "single virus" assay using RY5 cells. Medium containing oligonucleotide was added after infection. 2'-fluoro modified oligonucleotide 260 induced a dose-dependent inhibitory effect on HCV core protein expression (up to approximately 65% inhibition) even without pretreatment of cells with oligonucleotide before infection. In the same assay with pretreatment, 2'-fluoro P=S modified oligonucleotide 340 effectively inhibited HCV core protein expression at doses of 0.1 μM, 0.3 μM and 1.0 μM, with a maximum inhibition of about 75%. This oligonucleotide is therefore preferred. In the "single virus" assay using HepG2 cells, a dose-dependent inhibitory effect of oligonucleotide 340 as a uniform 2'-fluoro phosphorothioate was also observed (approximately 60% inhibition). This oligonucleotide is therefore preferred. The phosphorothioate oligonucleotide 260 also gave approximately 60% inhibition in the HepG2 cell assay.

Example 8

Diagnostic use of Oligonucleotides which inhibit HCV

Definitive diagnosis of HCV-caused hepatitis can be readily accomplished using antisense oligonucleotides which inhibit HCV RNA function, measurable as a decrease in HCV RNA levels or HCV core protein levels. RNA is extracted from blood samples or liver tissue samples obtained by needle biopsy, and electrophoresed and transferred to nitrocellulose for Northern blotting according to standard methods routinely used by those skilled in the art. An identical sample of blood or tissue is treated with antisense oligonucleotide prior to RNA extraction. The intensity of putative HCV signal in the two blots is then compared. If HCV is present (and presumably causative of disease), the HCV RNA signal will be reduced in the oligonucleotide-treated sample compared to the untreated sample. If HCV is not the cause of the disease, the two samples will have identical signals. Similar assays can be designed which employ other methods such as RT-PCR for HCV RNA detection and quantitation, or Western blotting or ELISA measurement of HCV core protein translation, all of which are routinely performed by those in the art.

Diagnostic methods using antisense oligonucleotides capable of inhibiting HCV RNA function are also useful for determining whether a given virus isolated from a patient with hepatitis will respond to treatment, before such treatment is initiated. RNA is isolated from a patient's blood or a liver tissue sample and blotted as described above. An identical sample of blood or tissue is treated with antisense oligonucleotide to inhibit HCV prior to RNA extraction and blotting. The intensity of putative HCV signal in the two blots is then compared. If the oligonucleotide is capable of inhibiting RNA function of the patient-derived virus, the HCV signal will be reduced in the oligonucleotide-treated sample compared to the untreated sample. This indicates that the patient's HCV infection is responsive to treatment with the antisense oligonucleotide, and a course of therapeutic treatment can be initiated. If the two samples have identical signals the oligonucleotide is not able to inhibit replication of the virus, and another method of treatment is indicated. Similar assays can be designed which employ other methods such as RT-PCR for RNA detection and quantitation, or Western blotting or ELISA for quantitation of HCV core protein expression, all of which are routinely performed by those in the art.

Example 9

The VHCV-IRES vaccinia/HCV Recombinant Virus Infected Mouse Model pSC11 (licensed from NIH) is a vaccinia virus expression vector that uses vaccinia early and late promotor P7.5 to express foreign genes, and vaccinia late promotor P11 to express a LacZ gene. The vaccinia viral thymidine kinase (TK) sequence flanked these two promoter-expression DNA arrangements for homologous recombination. HCV RNA nucleotides 1–1357, including the HCV 5' noncoding region, core and part of E1, obtained from pHCV3, a cDNA clone from a chronic HCV patient with HCV type H infection, was fused to the 5' end of a luciferase gene containing a SV40 polyadenylation signal sequence (Promega, pGL-2 promoter vector). The fused DNA fragment was placed under vaccinia promoter P7.5 of pSC11. The resultant construct was named pVNCELUA. A deletion of HCV RNA nucleotides 709 to 1357 was made in pVNCELUA and religation yielded the construct pVHCV-IRES. This construct uses the HCV initiator with the internal ribosome entry initiating mechanism for translation. pVC-LUA is a luciferase control virus construct in which the luciferase gene including the translation initiation codon and polyadenylation signal was directly placed under the P71.5 promoter of pSC11.

The basic experimental procedures for generating recombinant vaccinia virus by homologous recombination are known in the art. CV-1 cells for homologous recombination and viral plaque and Hu TK-143B for TK- selection were purchased from the ATCC. Plasmid DNA transfection was done using lipofectin (GIBCO BRL). The selection of recombinant virus was done by selection of viral plaques resistant to BrdU and demonstrating luciferase and β-galactosidase activity. The virus was purified through three rounds of plaque selection and used to prepare a 100% pure viral stock. The virus-containing BSC-40 cells were harvested in DMEM with 0.5% FBS followed by freeze-thawing three times to dissociate the virus. Cellular debris was centrifuged out and the supernatant was used for viral infection. A capital "V" was given to the name of each recombinant virus to distinguish it from the corresponding DNA construct (named with "p")

Six-week old female Balb/c mice were purchased from Charles River Laboratories (Boston Mass.). The mice were randomly grouped and were pretreated with oligonucleotide given subcutaneously once daily for two days before virus infection and post-treated once at 4 hours after infection. The infection was carried out by intraperitoneal injection of $1 \times 10^8$ pfu of virus in 0.5 ml saline solution. At 24 hours after infection the liver was taken from each mouse and kept on dry ice until it was homogenized at 30,000 rpm for about 30 seconds in 20 µl/mg luciferase reporter lysis buffer (Promega) using a Tissue Tearor (Biospec Products Inc.). Samples were transferred to eppendorf tubes on ice and shaken by vortex for 20 seconds followed by centrifuging at 4° C. for 3 minutes 20 µl of supernatant was transferred to a 96-well microtiter plate and 100 µl Luciferase Assay Reagent (Promega) was added. Immediately thereafter, the relative light units emitted were measured using a luminometer (ML 1000/Model 2.4, Dynatech Laboratories, Inc.).

Example 10

Evaluation of the 330 oligonucleotide ISIS 6547 in the VCHV-IRES infected mouse model:

A 20 mer deoxy oligonucleotide (the "330 oligonucleotide," SEQ ID NO: 6) targeted to nucleotides 330–349 surrounding the HCV translation initiation codon has been shown in previous examples to specifically inhibit HCV core protein synthesis in an in vitro translation assay, when tested as a phosphodiester. The phosphorothioate deoxyoligonucleotide of the same sequence, ISIS 6547 demonstrated at least a 50% reduction of HCV RNA when administered at dose of 100 nM to transformed human hepatocytes expressing HCV 5' noncoding region, core, and part of the E1 product (nucleotides 1–1357 of HCV). Hanecak et al., *J. Virol.* 1996, 70, 5203–5212. This effect was dose-dependent and sequence-dependent.

ISIS 6547 was evaluated in vivo using the VHCV-IRES infected mouse model. Eight female Balb/c mice were pretreated subcutaneously with oligonucleotide in saline once daily for two days, then infected intraperitoneally with $1 \times 10^8$ pfu VHCV-IRES followed by a post-treatment with oligonucleotide four hours after infection. A group treated with saline and infected with the same amount of VHCV-IRES served as controls. The effect of oligonucleotide on HCV gene expression was measured by luciferase activity at 24 hours after infection. When compared to luciferase activity from VHCV-IRES-infected but saline-treated controls, ISIS 6547 reduced luciferase signal in a dose-dependent manner, giving 10.5% inhibition at 2 mg/kg, 28.2% inhibition at 6 mg/kg and 51.9% inhibition at 20 mg/kg. In contrast, the unrelated control oligonucleotide ISIS 1082 (GCCGAGGTCCATGTCGTACGC; SEQ ID NO. 36) exhibited no inhibitory effect at lower doses, though non-specific inhibition of luciferase signal was observed at 20 mg/kg. Various routes of administration of oligonucleotide 6547 (subcutaneous, intravenous or intraperitoneal) gave similar levels of inhibition (76%, 63% and 58%, respectively, at 20 mg/kg).

Example 11

Evaluation of 5-methyl-C modified 330 oligonucleotide, ISIS 14803 in the VCHV-IRES infected mouse model One of the heterocyclic base modifications presently available is 5-methylcytosine (5-me-C) in which the nucleobase cytosine is methylated at the 5-position. The corresponding nucleotide is 5-methylcytidine. Oligonucleotides containing this modification demonstrate higher target binding affinity than analogs without the base modification, and are substrates for RNAse H. Dean and Griffey, Antisense and Nucleic Acid Drug Development 1997, 7, 229–233. They also elicit less immune stimulation and complement stimulation than unmodified versions. Henry et al., *Anti-Cancer Drug Design* 1997, 12, 409–412.

A 5-me-C version of ISIS 6547 was synthesized in which every cytidine nucleotide was replaced by a 5-methylcytidine. This oligonucleotide, ISIS 14803, was evaluated in the VHCV-IRES system in mice, in direct comparison to its parent compound, ISIS 6547. Eight female Balb/c mice were subcutaneously treated with oligonucleotide in saline at one day and two hours before infection and again at 4 hours after infection. Mice were infected by intraperitoneal injection with $1 \times 10^8$ pfu per mouse of VHCV-IRES or VC-LUA. At 24 hours after infection, luciferase activity in liver was determined and compared to luciferase activity in livers of a group of mice treated with saline and infected with the same amount of VHCV-IRES or VC-LUA. ISIS 14803 showed 11.1% inhibition of liver luciferase activity at 2 mg/kg, 33.5% inhibition at 6 mg/kg and 59.1% inhibition at 20 mg/kg. ISIS 14803 did not show any inhibition of luciferase activity in the control VC-LUA virus at the lower doses, though some nonspecific inhibition of luciferase activity was observed at the high dose of 20 mg/kg. Because this nonspecific inhibition was also observed with the control oligonucleotide, ISIS 1082, it was thought to be a general class effect of high doses of phosphorothioate oligonucleotides.

What is claimed is:

1. An antisense oligonucleotide up to 50 nucleotides in length which comprises at least a 5-nucleotide portion of SEQ ID NO:6 and which inhibits the function of HCV genomic or messenger RNA.

2. The antisense oligonucleotide of claim 1 which has at least one phosphorothioate backbone linkage.

3. The antisense oligonucleotide of claim 1 wherein at least one cytidine nucleotide is a 5'-methycytidine.

4. A composition comprising the antisense oligonucleotide of claim 1 and a pharmaceutically acceptable carrier.

5. The antisense oligonucleotide of claim 2 wherein every backbone linkage is a phosphorothioate backbone linkage and every cytidine nucleotide is a 5'-methylcytidine.

6. An antisense oligonucleotide comprising SEQ ID NO:6.

7. The antisense oligonucleotide of claim 6 which has at least one phosphorothioate backbone linkage.

8. The antisense oligonucleotide of claim 6 wherein at least one cytidine nucleotide is a 5-methylcytidine.

9. A composition comprising the oligonucleotide of claim 6 and pharmaceutically acceptable carrier.

10. A phosphorothioate oligodeoxynucleotide comprising SEQ ID NO:6 wherein every cytidine nucleotide is a 5'-methylcytidine.

11. A composition comprising the oligodeoxynucleotide of claim 10 and a pharmaceutically acceptable carrier.

* * * * *